US008951782B2

(12) United States Patent
Chang et al.

(10) Patent No.: US 8,951,782 B2
(45) Date of Patent: Feb. 10, 2015

(54) APPARATUS FOR SEPARATING CELLS USING MAGNETIC FORCE AND CELL SEPARATION METHOD USING THE SAME

(75) Inventors: Sung Hwan Chang, Daejeon (KR); Yeong-Eun Yoo, Daejeon (KR); Doo-Sun Choi, Daejeon (KR); Kyung-Hyun Whang, Daejeon (KR)

(73) Assignee: Korea Institute of Machinery & Materials, Daejeon (KR)

( * ) Notice: Subject to any disclaimer, the term of this patent is extended or adjusted under 35 U.S.C. 154(b) by 108 days.

(21) Appl. No.: 13/546,106

(22) Filed: Jul. 11, 2012

(65) Prior Publication Data

US 2013/0288226 A1   Oct. 31, 2013

(30) Foreign Application Priority Data

Apr. 30, 2012   (KR) .................. 10-2012-0045744

(51) Int. Cl.
*C12M 3/00*   (2006.01)
(52) U.S. Cl.
USPC ....... 435/288.5; 435/2; 435/283.1; 435/287.1
(58) Field of Classification Search
None
See application file for complete search history.

(56) References Cited

U.S. PATENT DOCUMENTS

2004/0018611 A1* 1/2004 Ward et al. ................. 435/287.2
2005/0274650 A1* 12/2005 Frazier et al. ................. 209/39

FOREIGN PATENT DOCUMENTS

KR   10-2007-0119785   12/2007
KR   10-2009-0088175   8/2009

OTHER PUBLICATIONS

Takayasu M et al. Continuous Magnetic Separation of Blood Components from Whole Blood, IEEE Trans Appl Superconduct, 10: 927-930, 2000.*
Iliescu C et al, Microfluidic device for continuous magnetophoretic separation of white blood cells, Microsyst Technol 15: 1157-1162, 2009.*

* cited by examiner

*Primary Examiner* — Satyendra Singh
(74) *Attorney, Agent, or Firm* — Lexyoume IP Meister, PLLC

(57) ABSTRACT

An apparatus for separating cells using magnetic force includes: a separation channel portion including ferromagnetic particles, and provided with a flow path through which a cell fluid containing a plurality of cells having at least one of diamagnetic and paramagnetic properties; and a magnetic field controller that generates a magnetic field within the flow path so that the cells in the cell fluid flow within the flow path and are separated by height by a magnetic field. Accordingly, there are provided an apparatus for separating cells using magnetic force and a cell separation method using the same, by which cells can be easily separated using magnetic force.

12 Claims, 8 Drawing Sheets

APPARATUS FOR SEPARATING CELLS USING MAGNETIC FORCE AND CELL SEPARATION METHOD USING THE SAME

CROSS-REFERENCE TO RELATED APPLICATION

This application claims priority to and the benefit of Korean Patent Application No. 10-2012-0045744 filed in the Korean Intellectual Property Office on Apr. 30, 2012, the entire contents of which are incorporated herein by reference.

BACKGROUND OF THE INVENTION (a) Field of the Invention

The present invention relates to an apparatus for separating cells using magnetic force and a cell separation method using the same, and more particularly, to an apparatus for separating cells using magnetic force and a cell separation method using the same, by which cells can be easily separated using magnetic force.

(b) Description of the Related Art

In general, a biochemical sample is in the form of a mixture of at least two types of materials. Thus, the separation technologies for analyzing a desired component or refining a particular component from a mixture are very important in a sample pretreatment step. Particularly, in the lab-on-a-chip concept, which involves integration of a micro flow channel, a mixer, a pump, and a valve on a chip and treatment of a small amount of sample at high speed and with high efficiency, a sample preparation process, such as refining and separating, is a core technology that has to be conducted prior to sub-analysis.

Moreover, cell-based diagnostics, which is important in biological or medical analysis, cell research, microbiological analysis, and tissue transplantation. With the recent development of cell research, cell analysis, and protein and DNA analysis techniques, studies on unifying and integrating such a clinical diagnostic procedure in the form of a microfluidic device are being conducted.

However, it was difficult to actually use conventional methods and apparatuses for separating cells using a micro flow channel because their cell separation performance did not meet expectations.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide an apparatus for separating cells using magnetic force and a cell separation method using the same.

An exemplary embodiment of the present invention provides an apparatus for separating cells using magnetic force, the apparatus including: a separation channel portion including ferromagnetic particles, and provided with a flow path through which a cell fluid containing a plurality of cells having at least one of diamagnetic and paramagnetic properties; and a magnetic field controller that generates a magnetic field within the flow path so that the cells in the cell fluid flow within the flow path and are separated by height by a magnetic field.

The separation channel portion may include: an upper substrate; and a lower substrate that is manufactured by hardening a mixed solution of ferromagnetic particles and polymer resin and constitutes the flow path by being coupled to the lower side of the upper substrate.

The flow path may include a microstructure in which a plurality of protrusions and a plurality of recesses interposed between the protrusions are formed in a repeated manner along the flow direction of the cell fluid in order to increase the gradient of the magnetic field.

The length of the protrusions and the length of the recesses may differ depending on the flow direction of the cell fluid.

The protrusions may be inclined at a slope with respect to the flow direction of the cell fluid.

A buffer fluid may be introduced into the flow path to prevent re-mixing of the cells after the cells are separated.

A pair of inlet openings communicating with the flow path and separated vertically may be formed on the ends of the separation channel portion, and the cell fluid and the buffer fluid may be introduced into the flow path through the pair of inlet openings, respectively.

A cell fluid containing red blood cells and white blood cells may be injected through the inlet opening at the upper side, and the buffer fluid may be injected through the inlet opening at the lower side.

The buffer fluid may be injected through the inlet opening at the upper side, and a cell fluid containing white blood cells and circulating tumor cells may be injected through the inlet opening at the lower side.

Differences in height between target cells may be controlled by adjusting the flow rate of the cell fluid in the flow path.

The magnetic field controller may include an electromagnet to adjust the intensity of a magnetic field by controlling applied currents.

An exemplary embodiment of the present invention provides a method for separating cells using magnetic force, the method including: injecting a cell fluid into a flow path; generating a magnetic field so that a plurality of cells contained in the cell fluid flowing within the flow path are separated by height; and discharging the separated cells.

The method may further include injecting a buffer fluid into the flow path after the injection of a cell fluid.

In the injection of a cell fluid, a cell fluid containing red blood cells and white blood cells may be injected into an upper part of the flow path, and in the injection of a buffer fluid, the buffer fluid may be injected into a lower part of the flow path.

In the injection of a cell fluid, a cell fluid containing circulating tumor cells and white blood cells may be injected into a lower part of the flow path, and in the injection of a buffer fluid, the buffer fluid may be injected into an upper part of the flow path.

According to the present invention, there is provided an apparatus for separating cells using magnetic force, by which cells can be easily separated using magnetic force.

Moreover, a magnetic field can be easily generated by including ferromagnetic particles in the separation channel portion.

Furthermore, it is possible to prevent separated cells from being re-mixed together within the flow path by injecting a buffer fluid into the flow path.

In addition, cell separation performance can be improved by increasing the gradient of a magnetic field generated by forming protrusions within the flow path.

Besides, the force applied to the cells by a magnetic field can be further increased by adjusting the lengths of protrusions and recesses formed within the flow path.

DETAILED DESCRIPTION OF THE EMBODIMENTS

Figure 1:
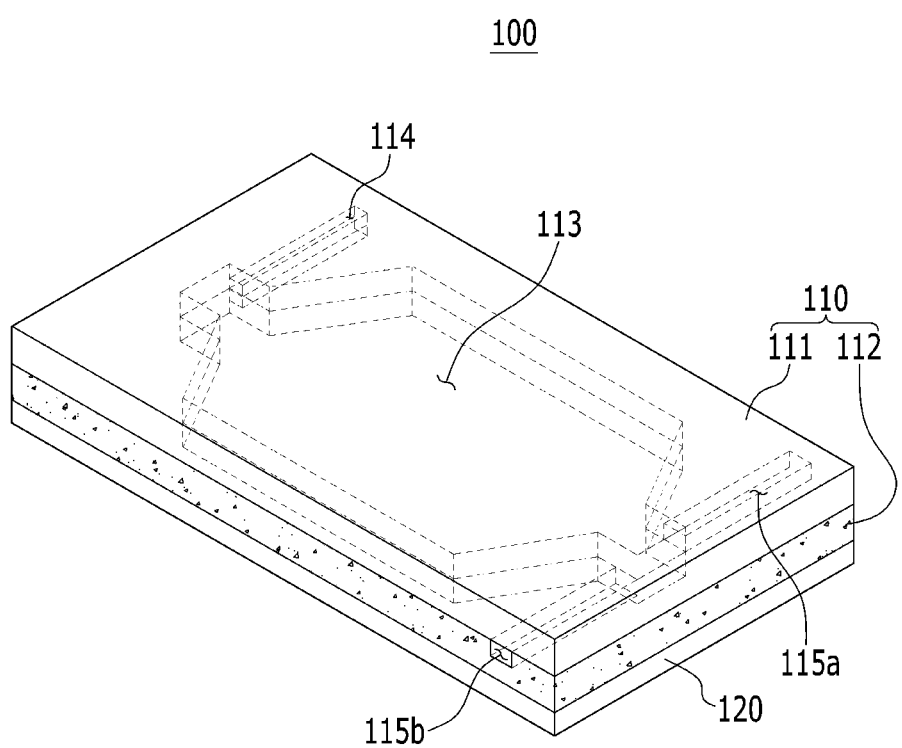
FIG. 1 is a schematic perspective view of a cell separation apparatus using magnetic force according to a first exemplary embodiment of the present invention.

In several exemplary embodiments, constituent elements having the same configuration are representatively described in a first exemplary embodiment by using the same reference numeral and only constituent elements other than the constituent elements described in the first exemplary embodiment will be described in other embodiments.

Hereinafter, a cell separation apparatus 100 using magnetic force according to a first exemplary embodiment of the present invention will be described in detail with reference to the accompanying drawings.

Figure 2:
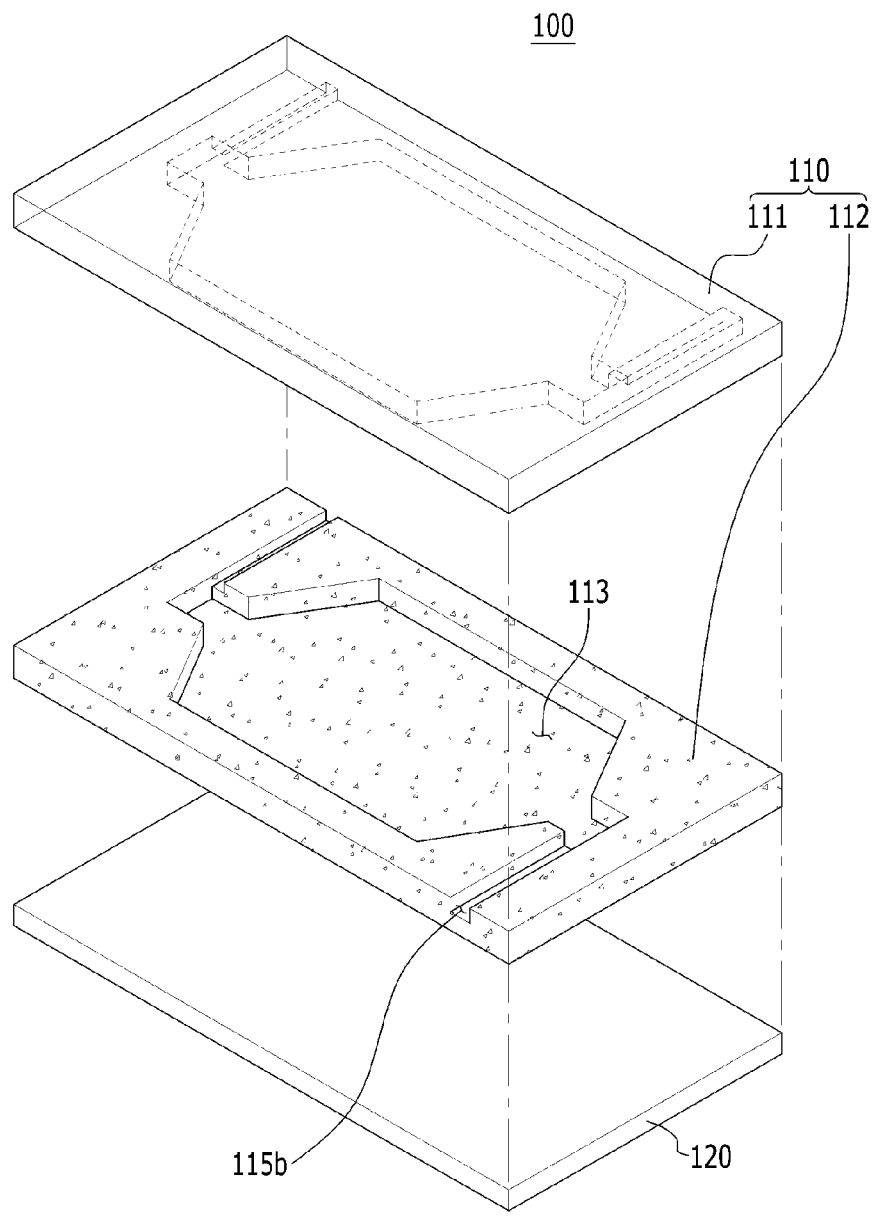
FIG. 2 is a schematic exploded perspective view of the cell separation apparatus using magnetic force of FIG. 1.

FIG. 1 is a schematic perspective view of a cell separation apparatus using magnetic force according to a first exemplary embodiment of the present invention. FIG. 2 is a schematic exploded perspective view of the cell separation apparatus using magnetic force of FIG. 1.

Referring to FIG. 1 and FIG. 2, the cell separation apparatus 100 using magnetic force according to the first exemplary embodiment of the present invention concerns an apparatus which generates a magnetic field by interactions between ferromagnetic particles P and a magnetic field controller to separate cells using the force applied to the cells from the magnetic field, and includes a separation channel portion 110 and a magnetic field controller 120.

The separation channel portion 110 is a member that constitutes a flow path 113 for separating cells by allowing a cell fluid containing target cells to flow, and includes an upper substrate 111 and a lower substrate 112.

The upper substrate 111 is joined to the lower substrate 112, which is to be described later, to constitute the flow path 113 for allowing the cell fluid to flow. It takes the form of a flat plate, and has an inwardly recessed region on the bottom surface.

In the present exemplary embodiment, the upper substrate 111 may be made of PDMS (PolyDimethylSiloxane), PTFE (polytetrafluroethylene), PMMA (PolyMethylMethcrylate), or COC (Cyclic Olefin Copolymer), but is not limited thereto if it is a general polymer material.

The lower substrate 112 is coupled to the lower side of the upper substrate 111. It takes the form of a flat plate, and has an inwardly recessed region on the top surface.

Preferably, the lower substrate 112 is formed and manufactured by hardening a mixed solution of polymer resin and ferromagnetic particles P such that the ferromagnetic particles P are uniformly distributed within the lower substrate 112.

The polymer resin used as the material of the lower substrate 112 may be identical to those for the upper substrate 111. The ferromagnetic particles P may be nano or micro particles of nickel (Ni), cobalt (Co), iron (Fe), etc.

Accordingly, the separation channel portion 110 manufactured by coupling the upper substrate 111 and the lower substrate 112 includes the flow path 113 formed therein, an inlet opening 114, a passage for introducing a cell fluid by communication with the separation channel portion 110, formed on the front end, a first outlet opening 115a formed at an upper part of the rear end and discharging cells, separated and flowing in the upper part within the cell fluid, and a second outlet opening 115b formed at a lower part of the rear end and discharging cells flowing in the lower part.

That is, the inlet opening 114 for putting in a cell fluid is provided on the front end of the separation channel portion 110, the first outlet opening 115a for discharging cells moving upward by a magnetic field within the flow path 113 is formed on the rear end of the separation channel portion 110, and the second outlet opening 115b is formed below the first outlet opening 115a.

The magnetic field controller 120 is a member that is provided under the separation channel portion 110 and generates a magnetic field in the flow path 113 by reacting with the ferromagnetic particles P of the lower substrate 112. In this exemplary embodiment, the magnetic field controller 120 may be provided in the form of an electromagnet to control magnetic intensity and action so that the overall intensity of the magnetic field is adjusted by adjusting the amount of applied current. However, the form of the magnetic field controller 120 is not limited thereto but may be provided in the form of a permanent magnet.

A cell separation method using the above-described cell separation apparatus using magnetic force according to the first exemplary embodiment will now be described.

1. Separation of Red Blood Cells and White Blood Cells

Figure 3:
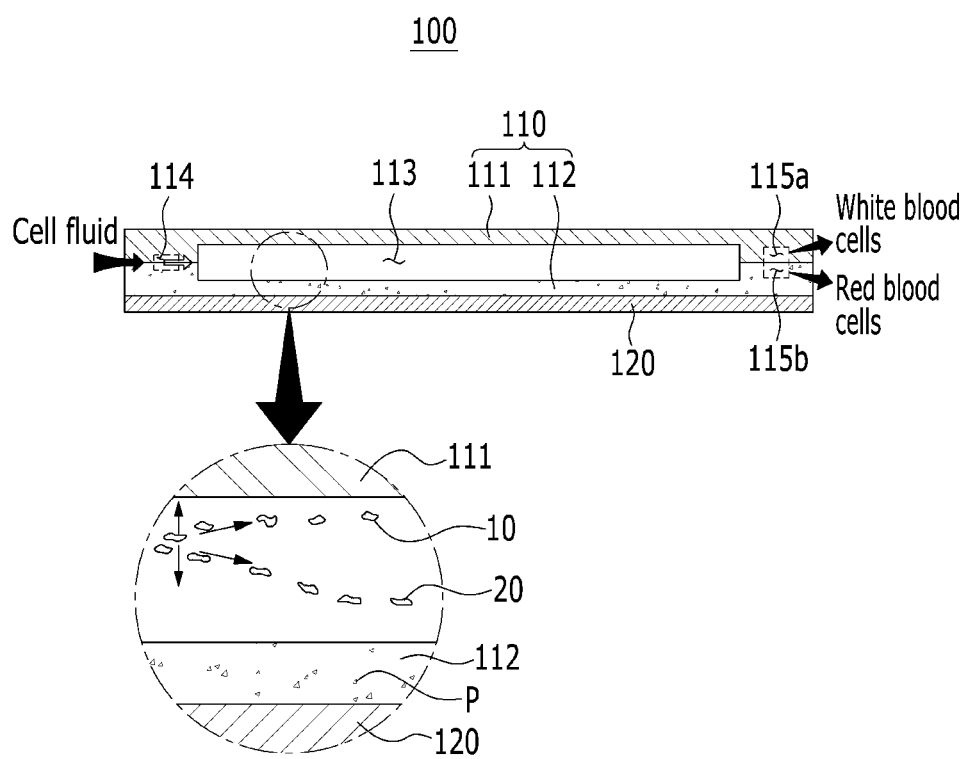
FIG. 3 schematically illustrates an operation of separating white blood cells and red blood cells by the cell separation apparatus using magnetic force of FIG. 1.

FIG. 3 schematically illustrates an operation of separating white blood cells and red blood cells by the cell separation apparatus using magnetic force of FIG. 1.

Referring to FIG. 3, first of all, the cell separation apparatus 100 using magnetic force of the present exemplary embodiment is described as separating white blood cells 10 and red blood cells 20 in a cell fluid, which are targeted for separation.

First, when the cell fluid is injected into the flow path 113 through the inlet opening 114, the cell fluid flows through the flow path 113. At the same time, the magnetic field 120 is operated to generate a magnetic field within the flow path 113 by reacting with the ferromagnetic particles P uniformly distributed in the lower substrate 112.

The red blood cells 20, which are paramagnetic particles, move and flow toward the lower substrate 112 by the magnetic field generated in the flow path 113, and the white blood cells 10, which are diamagnetic particles, move toward the upper substrate 111.

In other words, the white blood cells 10 flow within the flow path 113, being magnetized by a magnetic field and moved toward the lower substrate 112, and the paramagnetic red blood cells 20 move toward a lower part of the flow path 113 by a magnetic field formed extending from the lower part to an upper part of the flow path 113, while flowing within the flow path 113.

Along with continuous flow of the cell fluid, the white blood cells 10 in the upper part of the flow path 113 are collected through the first outlet opening 115a and discharged to the outside, and the red blood cells 20 flowing in the lower part of the flow path 113 are collected through the second outlet opening 115b and discharged to the outside. As a result, the red blood cells 20 and the white blood cells 10 can be separated.

2. Separation of Circulating Tumor Cells and White Blood Cells

A method for separating white blood cells 10 and circulating tumor cells 30, both of which having the same diamagnetism and contained in a cell fluid according to this exemplary embodiment will be described. First of all, the cell fluid containing the white blood cells 10 and the circulating tumor cells 30 is made to flow in the flow path.

At the same time, the ferromagnetic particles P in the lower substrate 112 and the magnetic field controller 120 are used to generate a magnetic field within the flow path 113.

$$F_{cell} = \frac{1}{2}\frac{\Delta_\chi \cdot V_{cell}}{\mu_0}\nabla |B|^2 \quad \text{(Equation 1)}$$

($F_{cell}$: force applied to cells, $V_{cell}$: cell volume, $\nabla|B|$: magnetic field gradient, $\Delta\chi$: difference in magnetic susceptibility between cells and cell fluid, and $\mu_0$: magnetic permeability in vacuum)

As in Equation 1, the force $F_{cell}$ applied to the cells by a magnetic field is proportional to the volume $V_{cell}$ of the cells. In general, the circulating tumor cells (CTC) 30 having a diameter of around 18 μm and a relatively large volume are pushed upward from the lower substrate 112 by a magnetic field further than the white blood cells 10 having a diameter of around 10 μm and a relatively small volume, the circulating tumor cells 30 move toward the upper substrate 111 and flow in the flow path 113, and the white blood cells 10 move toward the lower substrate 112, being adjacent to it.

Accordingly, the circulating tumor cells 30 can be collected and separated through the first outlet opening 115a, and the white red cells 10 can be collected and separated through the second outlet opening 115b.

Meanwhile, when separating a plurality of cells having the same diamagnetic properties, as in this case, the distances between different types of cells reaching the outlet openings can be further extended by increasing the length of the separation channel portion 110 or adjusting the flow rate of the cell fluid.

Next, a cell separation apparatus 200 using magnetic force according to a second exemplary embodiment of the present invention will be described.

Figure 4:
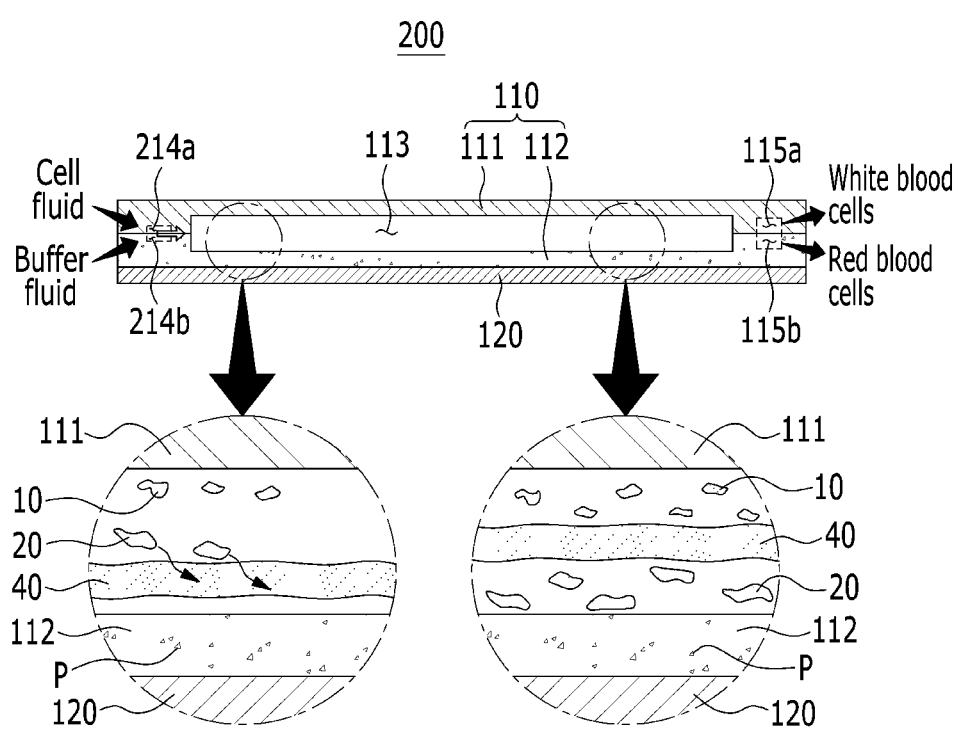
FIG. 4 schematically illustrates an operation of separating white blood cells and red blood cells by a cell separation apparatus using magnetic force according to the second exemplary embodiment of the present invention, FIG. 5 schematically illustrates an operation of separating white blood cells and circulating tumor cells by the cell separation apparatus using magnetic force according to the second exemplary embodiment of the present invention.

FIG. 4 schematically illustrates an operation of separating white blood cells and red blood cells by a cell separation apparatus using magnetic force according to the second exemplary embodiment of the present invention.

Referring to FIG. 4, the cell separation apparatus 200 using magnetic force according to the second exemplary embodiment of the present invention includes a separation channel portion 110 and a magnetic field controller 120. The magnetic field controller 120 of the present exemplary embodiment has the same configuration as the first exemplary embodiment, so redundant description will be omitted.

The separation channel portion 110 has the same configuration as the first exemplary embodiment, and includes an upper substrate 111 and a lower substrate 112. However, a first inlet opening 214a is formed at an upper part of the front end of the separation channel portion 110, and a second inlet opening 214b is formed at a lower part thereof.

Hereinafter, a cell separation method using the cell separation apparatus 200 using magnetic force according to the present exemplary embodiment will be described.

In the present exemplary embodiment, unlike the first exemplary embodiment, a cell fluid targeted for separation and a buffer fluid 40 are simultaneously introduced into a flow path 113, thereby improving cell separation performance. The following description will be given with respect to the case where white blood cells 10 and red blood cells 20 are target cells in the cell fluid and the case where white blood cells 10 and circulating tumor cells 30 are target cells in the cell fluid.

1. Separation of Red Blood Cells and White Blood Cells

First, referring to FIG. 4, the cell fluid containing the white blood cells 10 and the red blood cells 20 is made to flow into the flow path 113 through a first inlet opening 214a, which is disposed at an upper side.

Simultaneously with the introduction of the cell fluid, a buffer fluid 40 is made to flow into the flow path 113 through a second opening 214b positioned to be lower than the first inlet opening 214a. The buffer fluid 40 used in the present exemplary embodiment may be, but not limited to, PBS (Phosphate Buffer Silane).

At the same time, when the magnetic field controller 120 is operated to generate a magnetic field within the flow path 113, the diamagnetic red blood cells 10 are pushed from the lower substrate 112 by a magnetic formed toward the upper substrate 111 while flowing in the flow path 113, and flow therein, with an upper part of the flow path 113 adjacent thereto. The paramagnetic red blood cells 20 are moved toward the lower substrate 112 by a magnetic field and transmitted through the buffer fluid 40 below them, and flow therein, with the lower substrate 112 under the flow path 113 adjacent thereto.

Accordingly, the buffer fluid 40 injected separately through the second inlet opening 214a flows in a space between the white blood cells 10 and the red blood cells 20, which flow in the flow path 113, being separated from each other. Consequently, the white blood cells 10 and red blood cells 20, which flow in the flow path 113, spaced apart from each other, can be prevented from being re-mixed together due to diffusion or random flow, and the accuracy and performance of cell separation can be improved.

2. Separation of Circulating Tumor Cells and White Blood Cells

Figure 5:
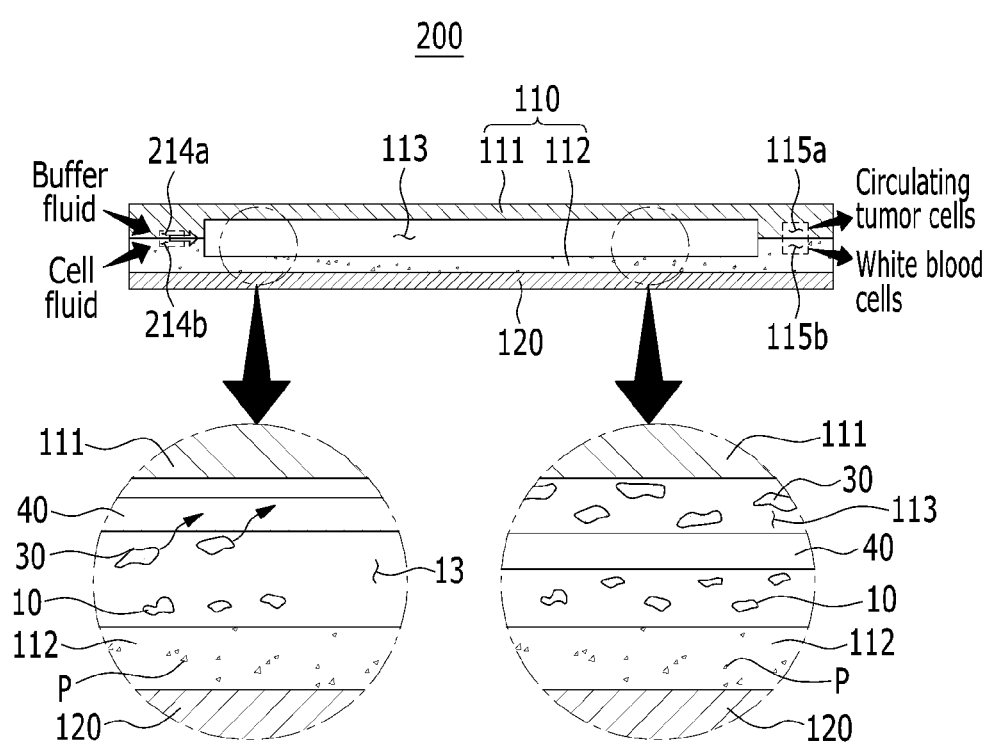

FIG. 5 schematically illustrates an operation of separating white blood cells 10 and circulating tumor cells 30 by the cell separation apparatus 200 using magnetic force according to the second exemplary embodiment of the present invention.

Referring to FIG. 5, in the case that diagmagnetic circulating tumor cells 30 and paramagnetic white blood cells 10, which are contained in a cell fluid, are separated, the cell fluid is introduced through the second inlet opening 214b at the lower side to flow within the flow path 113.

Simultaneously with the introduction of the cell fluid, the buffer fluid 40 is made to flow into the flow path 113 through the first inlet opening 214a positioned above the second inlet opening 214b.

At the same time, when the magnetic field controller 120 is operated to generate a magnetic field within the flow path 113, the circulating tumor cells 30 having a larger volume are more affected by a magnetic field than the white blood cells 10 having a smaller volume and strongly pushed toward the upper substrate 111. At this point, the circulating tumor cells 30 are transmitted through the buffer fluid 40 injected through the first inlet opening 214a and flow in an upper part of the buffer fluid, that is, in a position adjacent to the upper substrate 111.

The buffer fluid 40 separately injected through the first inlet opening 214a flows in a space between the circulating tumor cells 30 and the white blood cells 10, which flow within the flow path 113, being spaced apart from each other. Consequently, the circulating tumor cells 30 and the white blood cells 10, separated from each other, can be prevented from being re-mixed together due to diffusion or random flow, and the accuracy and performance of cell separation can be improved.

In this exemplary embodiment, the positions at which the buffer fluid and the cell fluid are introduced are not limited to the above description, but may be determined by comprehensively taking into account the type of the buffer fluid and the type and size of target cells.

Next, a cell separation apparatus 300 using magnetic force according to a third exemplary embodiment of the present invention will be described.

Figure 6:
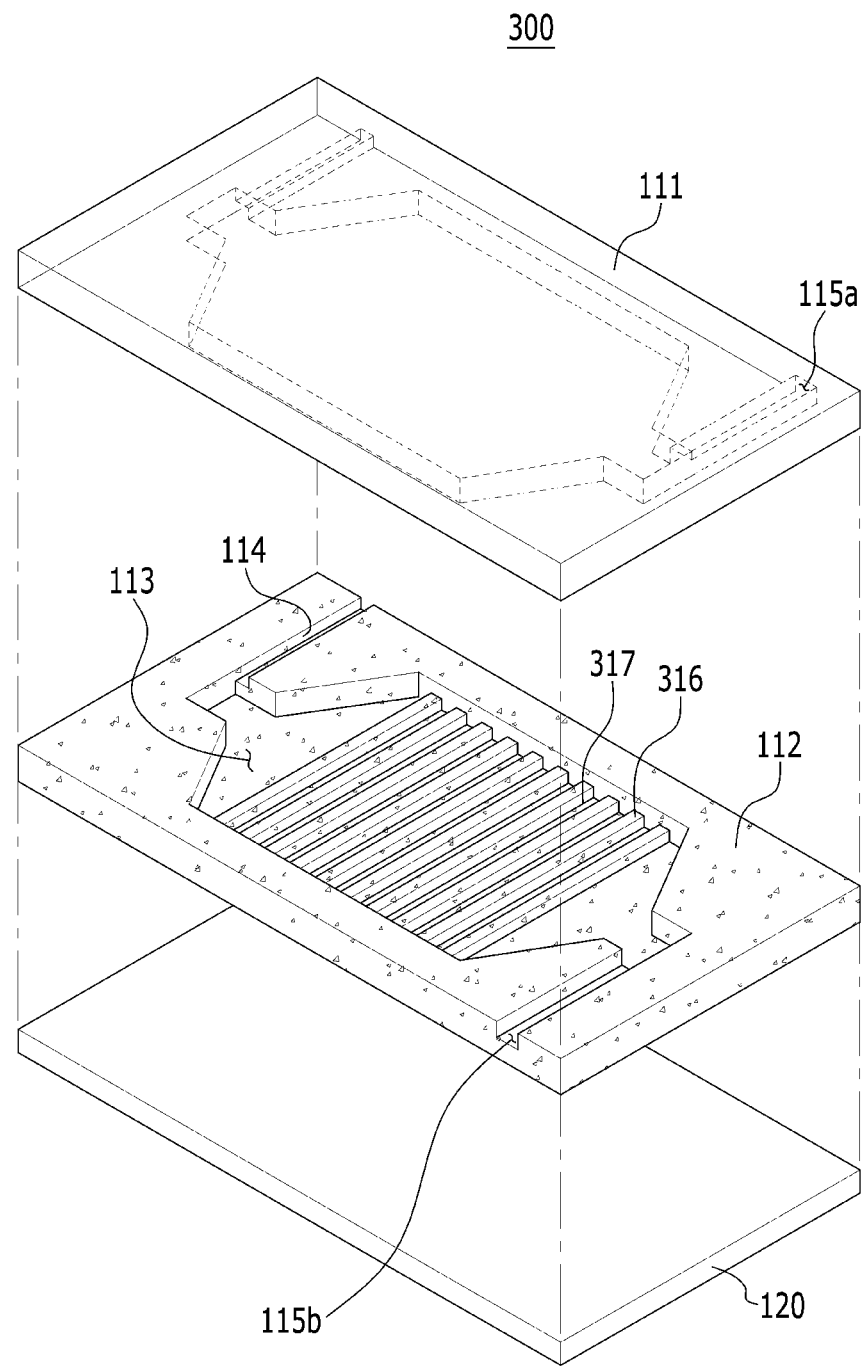
FIG. 6 is a schematic exploded perspective view of a cell separation apparatus using magnetic force according to a third exemplary embodiment of the present invention.

FIG. 6 is a schematic exploded perspective view of a cell separation apparatus using magnetic force according to a third exemplary embodiment of the present invention.

Referring to FIG. 6, the cell separation apparatus 300 using magnetic force according to the third exemplary embodiment of the present invention includes a separation channel portion 110 and a magnetic field controller 120. The magnetic field controller 120 of the present exemplary embodiment has the same configuration as the first exemplary embodiment, so redundant description will be omitted.

The separation channel portion 110 includes an upper substrate 111 and a lower substrate 112. The upper substrate 111 has the same configuration as the first exemplary embodiment, so redundant description will be omitted.

The lower substrate 112 is coupled to the lower side of the upper substrate 111. It has an inwardly recessed region on the top surface. The lower substrate 112 is manufactured by hardening a mixed solution of polymer resin and ferromagnetic particles P such that the ferromagnetic particles P are uniformly distributed within the lower substrate 112.

A plurality of protrusions 316 and a plurality of recesses 317 are repeated formed in an alternating manner along the flow direction of a cell fluid in the recessed region of the lower substrate 112, i.e., a top surface region of the lower substrate 112 that is coupled to the upper substrate 111 to constitute a flow path 113.

The plurality of protrusions 316 protrude upward from the lower substrate 112, the recesses 317, recessed lower than the height of the protrusions 316 to be described later, are formed between the neighboring protrusions 316, and the shape of a cross-section taken along the flow direction of the cell fluid is rectangular.

The recesses 317, recessed from the protrusions 316, are spaced apart from each other and formed between the neighboring protrusions 317.

In the present exemplary embodiment, the protrusions 316 and the recesses 317 are formed integrally with the lower substrate 112, and are manufactured of a mixed solution of polymer resin and ferromagnetic particles P. In a modification, the lower substrate 112 and the protrusions 316 may be separately provided and coupled together.

The gradient of a magnetic field generated within the flow path 113 by the magnetic field controller 120 differs depending on the shapes, lengths, sizes, etc. of the protrusions 316 and the recesses 317. Therefore, the specifications of the protrusions 316 and recesses 317 are determined by comprehensively taking into account the above-description.

Hereinafter, a cell separation method using the cell separation apparatus 300 using magnetic force according to the present exemplary embodiment will be described by taking, as an example, the case where the white blood cells 10 and the red blood cells 20 are target cells.

Figure 7:
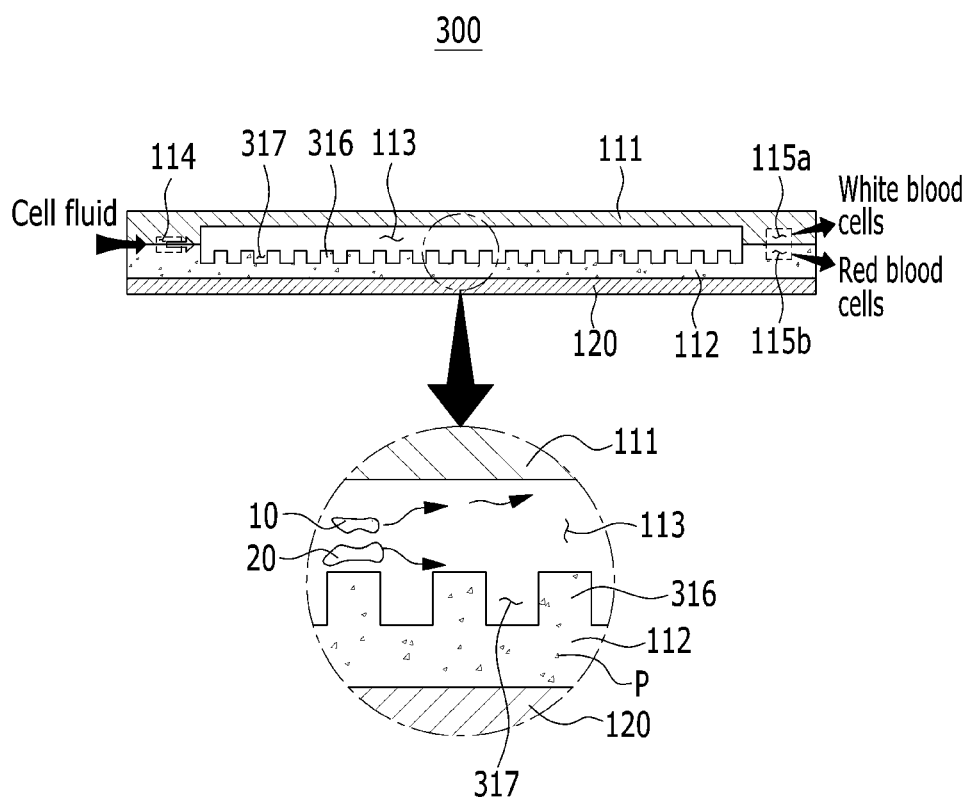
FIG. 7 schematically illustrates an operation of separating white blood cells and red blood cells using the cell separation apparatus using magnetic force of FIG. 6.

FIG. 7 schematically illustrates an operation of separating white blood cells and red blood cells using the cell separation apparatus using magnetic force of FIG. 6.

First, as shown in FIG. 7, a cell fluid containing white blood cells 10 and red blood cells 20 is made to flow into a flow path 113 through an inlet opening 114.

At the same time, when the magnetic field controller 120 is operated to generate a magnetic field within the flow path 113, the diamagnetic red blood cells 10 are pushed from the lower substrate 112 by a magnetic formed toward the upper substrate 111 while flowing in the flow path 113, and flow in an upper part of the flow path 113. The paramagnetic red blood cells 20 are moved toward the lower substrate 112 by a magnetic field and flow in a lower part of the flow path 113, i.e., in a position adjacent to the lower substrate 112.

Meanwhile, the gradient $\nabla |B|^2$ of a magnetic field increases due to the protrusions 316 and recesses 317 that are formed in a repeated manner within the flow path 113. The diamagnetic white blood cells 10 and the paramagnetic red blood cells 20 receive much more force by the increased magnetic field gradient, as shown in Equation 1, and move upward and downward within the flow path.

Accordingly, with the increase of the magnetic field gradient due to the microstructure of the protrusions 316 and the recesses 317, the force applied to the white blood cells 10 and the red blood cells 20 also increases. As a result, the distances between different types of cells become larger, thereby enabling precise and rapid cell separation.

Next, a cell separation apparatus 400 using magnetic force according to a fourth exemplary embodiment of the present invention will be described.

Figure 8:
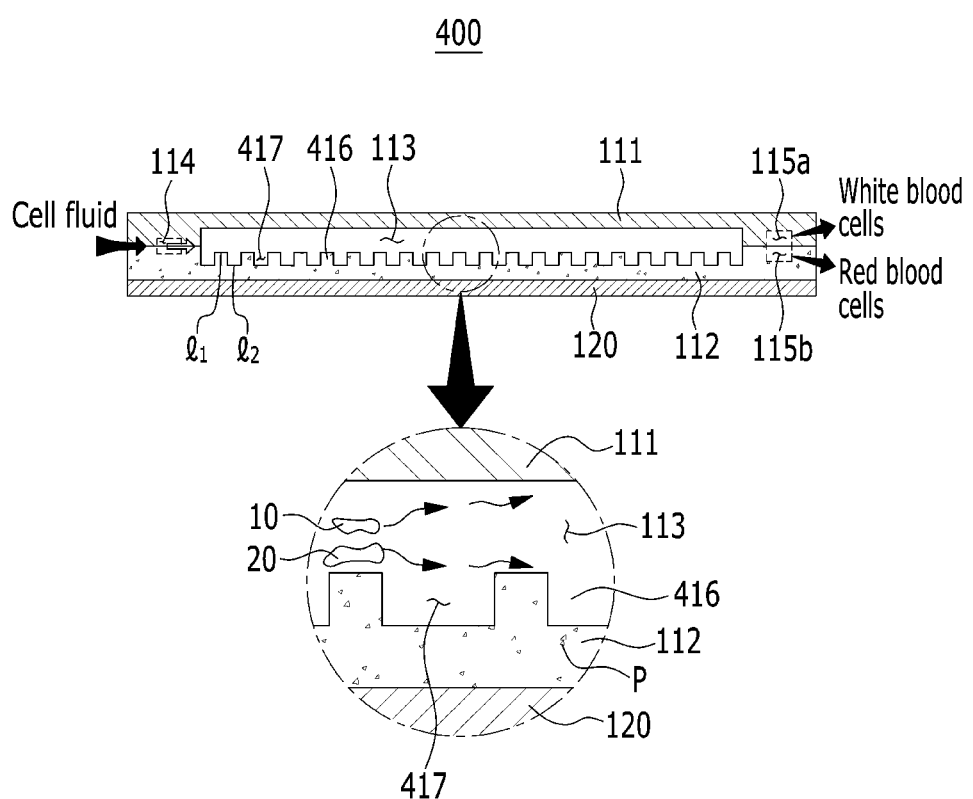
FIG. 8 schematically illustrates an operation of separating white blood cells and red blood cells using a cell separation apparatus using magnetic force according to a fourth exemplary embodiment of the present invention.

FIG. 8 schematically illustrates an operation of separating white blood cells and red blood cells using a cell separation apparatus using magnetic force according to a fourth exemplary embodiment of the present invention.

Referring to FIG. 8, the cell separation apparatus 400 using magnetic force according to the fourth exemplary embodiment of the present invention includes a separation channel portion 110 and a magnetic field controller 120. The separation channel portion 110 and magnetic field controller 120 of the present exemplary embodiment have the same configurations as the third exemplary embodiment, so redundant description will be omitted.

In the present exemplary embodiment, however, the length $l_1$ of protrusions 416 is shorter than the length $l_2$ of recesses 417 along the flow direction of the cell fluid so that an increase in the amount of cells caused by the gradient of a magnetic field generated by the protrusions 416 is greater than a decrease in the amount of cells caused by the gradient of a magnetic field generated by the recesses 417. In the present exemplary embodiment, the ratio of the length $l_1$ of the protrusions 416 to the length $l_2$ of the recesses 417 is 1:2, but the present invention is not limited thereto.

Hereinafter, a cell separation method using the cell separation apparatus 400 using magnetic force according to the present exemplary embodiment will be described by taking, as an example, the case where white blood cells 10 and red blood cells 20, which are targets for separation, are contained in the cell fluid.

First, as shown in FIG. 8, a cell fluid containing white blood cells 10 and red blood cells 20 is made to flow into a flow path 113 through an inlet opening 114.

At the same time, when the magnetic field controller 120 is operated to generate a magnetic field within the flow path 113, the diamagnetic red blood cells 10 are pushed from the lower substrate 112 by a magnetic formed toward the upper substrate 111 while flowing in the flow path 113, and flow in an upper part of the flow path 113. The paramagnetic red blood cells 20 are moved toward the lower substrate 112 by a magnetic field and flow in a lower part of the flow path 113.

Meanwhile, the gradient of a magnetic field increases due to the protrusions 316 and recesses 317 that are formed in a repeated manner within the flow path 113. The diamagnetic white blood cells 10 and the paramagnetic red blood cells 20 receive much more force by the increased magnetic field gradient, as shown in Equation 1, and move upward and downward within the flow path.

The movement of cells by a microstructure according to the present exemplary embodiment will be described in detail. The white blood cells 10 rise by the increase of the gradient of the magnetic field formed by the protrusions 416 when passing through above the protrusions 416, while the white blood cells 10 fall when passing through the recesses 417.

At this point, a larger amount of white blood cells 10 rises by higher force caused by the protrusions 416 having a shorter length $l_1$, whereas a smaller amount of white blood cells 10 than the amount that rises by the protrusions 416 falls by lower force caused by the recesses 417.

Accordingly, by forming the length $l_2$ of the recesses 417 to be greater than the length $l_1$ of the protrusions 416, a large amount of diamagnetic white blood cells 10 rises because the fall thereof caused by the recesses 417 is compensated for, and they can be separated from the paramagnetic red blood cells 10 at a large distance.

The scope of the present invention is not limited to the above-described exemplary embodiment, but may be carried out in various embodiments within the scope of the appended claims. It will be clear to one skilled in the art that changes or modifications may be made without deviating from the gist of this invention and such changes and modifications are deemed to fall within the scope of the claims below.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

<Description of symbols>

| | |
|---|---|
| 100: cell separation apparatus using magnetic force according to first exemplary embodiment of present invention | |
| 110: separation channel portion | 111: upper substrate |
| 112: lower substrate | 113: flow path |
| 114: inlet opening | 115: outlet opening |
| 120: magnetic field controller | |

What is claimed is:

1. An apparatus for separating cells using magnetic force, the apparatus comprising:
a separation channel portion including an upper substrate, and a lower substrate that is manufactured by hardening a mixed solution of ferromagnetic particles and polymer resin such that the ferromagnetic particles are distributed within the lower substrate, and provided with a flow path through which a cell fluid containing a plurality of cells having at least one of diamagnetic and paramagnetic properties passes through by being coupled to the lower side of the upper substrate;
an inlet opening, a passage for introducing the cell fluid by communication with the separation channel portion, formed on the front end of the separation channel;
a first outlet opening formed at an upper part of the rear end of the separation channel and discharging cells, separated and flowing in the upper part of the separation channel within the cell fluid;
a second outlet opening formed at a lower part of the rear end of the separation channel and discharging cells flowing in the lower part of the separation channel; and
a magnetic field controller that generates a magnetic field within the flow path so that the cells in the cell fluid flow within the flow path and are separated by height by the magnetic field,
wherein the flow path comprises a microstructure in which a plurality of protrusions and a plurality of recesses interposed between the protrusions are formed in a repeated manner along the flow direction of the cell fluid and extend so that the protrusions and recesses intersect with the flow direction of the cell fluid in order to increase the gradient of the magnetic field,
wherein the length of the protrusions and the length of the recesses differ depending on the flow direction of the cell fluid, and the ratio of the length of the protrusions to the length of the recesses is 1:2.

2. The apparatus of claim 1, wherein the protrusions are inclined at a slope with respect to the flow direction of the cell fluid.

3. The apparatus of claim 1, wherein a buffer fluid is introduced into the flow path to prevent re-mixing of the cells after the cells are separated.

4. The apparatus of claim 3, wherein
a pair of inlet openings communicating with the flow path and separated vertically are formed on the ends of the separation channel portion, and
the cell fluid and the buffer fluid are introduced into the flow path through the pair of inlet openings, respectively.

5. The apparatus of claim 4, wherein the cell fluid comprises red blood cells and white blood cells, and is injected through the inlet opening at the upper side, and the buffer fluid is injected through the inlet opening at the lower side.

6. The apparatus of claim 4, wherein the buffer fluid is injected through the inlet opening at the upper side, and wherein the cell fluid comprises white blood cells and circulating tumor cells, and is injected through the inlet opening at the lower side.

7. The apparatus of claim 1, wherein differences in height between target cells are controlled by adjusting the flow rate of the cell fluid in the flow path.

8. The apparatus of claim 1, wherein the magnetic field controller comprises an electromagnet to adjust the intensity of a magnetic field by controlling applied currents.

9. A method for separating cells by magnetic force with the apparatus as set forth in claim 1, the method comprising:
injecting a cell fluid into the flow path of the apparatus of claim 1;

generating a magnetic field so that a plurality of cells contained in the cell fluid flowing within the flow path are separated by height; and discharging the separated cells.

10. The method of claim 9, further comprising injecting a buffer fluid into the flow path after the injection of the cell fluid.

11. The method of claim 10, wherein, in the injection of a cell fluid, the cell fluid comprises red blood cells and white blood cells, and is injected into an upper part of the flow path, and in the injection of a buffer fluid, the buffer fluid is injected into a lower part of the flow path.

12. The method of claim 10, wherein, in the injection of a cell fluid, the cell fluid comprises circulating tumor cells and white blood cells, and is injected into a lower part of the flow path, and in the injection of a buffer fluid, the buffer fluid is injected into an upper part of the flow path.

* * * * *